United States Patent
Abell et al.

(10) Patent No.: US 9,422,067 B2
(45) Date of Patent: Aug. 23, 2016

(54) METHOD OF PROVIDING A CHEMICAL OR BIOLOGICAL MATERIAL IN QUANTISED FORM AND SYSTEM THEREFOR

(75) Inventors: Chris Abell, Cambridge (GB); Wilhelm T. S. Huck, Cambridge (GB); Frank F. Craig, Cambridge (GB)

(73) Assignee: SPHERE FLUIDICS LIMITED, Cambridge (GB)

( * ) Notice: Subject to any disclaimer, the term of this patent is extended or adjusted under 35 U.S.C. 154(b) by 711 days.

(21) Appl. No.: 13/812,891

(22) PCT Filed: Aug. 17, 2011

(86) PCT No.: PCT/GB2011/051552
§ 371 (c)(1),
(2), (4) Date: Feb. 15, 2013

(87) PCT Pub. No.: WO2012/022976
PCT Pub. Date: Feb. 23, 2012

(65) Prior Publication Data
US 2013/0139477 A1    Jun. 6, 2013

(30) Foreign Application Priority Data
Aug. 20, 2010   (GB) .................................. 1013969.9

(51) Int. Cl.
| | | |
|---|---|---|
| B65B 3/04 | (2006.01) | |
| B65D 79/00 | (2006.01) | |
| B65D 81/00 | (2006.01) | |
| C12N 1/04 | (2006.01) | |
| C12N 9/96 | (2006.01) | |
| B65B 3/00 | (2006.01) | |

(52) U.S. Cl.
CPC . *B65B 3/04* (2013.01); *B65D 79/00* (2013.01); *B65D 81/00* (2013.01); *C12N 1/04* (2013.01); *C12N 9/96* (2013.01); *B65B 3/003* (2013.01)

(58) Field of Classification Search
None
See application file for complete search history.

(56) References Cited

U.S. PATENT DOCUMENTS

| | | | | |
|---|---|---|---|---|
| 4,987,154 A | * | 1/1991 | Long, Jr. .............. | A61K 9/0026 424/9.37 |
| 6,627,603 B1 | | 9/2003 | Bibbette | |
| 6,855,296 B1 | | 2/2005 | Baker et al. | |
| 2005/0112186 A1 | * | 5/2005 | Devore .................. | A61K 31/00 424/450 |
| 2007/0197475 A1 | * | 8/2007 | Kuznetsova ......... | A61K 9/0026 514/78 |
| 2008/0075757 A1 | | 3/2008 | Chauhan et al. | |
| 2009/0010890 A1 | * | 1/2009 | VanderGheynst ..... | A61K 9/107 424/93.4 |
| 2009/0012187 A1 | * | 1/2009 | Chu ....................... | A61K 9/113 516/54 |
| 2010/0022414 A1 | * | 1/2010 | Link ..................... | B01F 3/0807 506/18 |
| 2011/0305761 A1 | * | 12/2011 | Shum ................... | A61K 9/1273 424/489 |

FOREIGN PATENT DOCUMENTS

| | | |
|---|---|---|
| WO | 2009050512 | 4/2009 |
| WO | 2010009365 | 1/2010 |
| WO | WO 2010009365 A1 * | 1/2010 |

OTHER PUBLICATIONS

Balagadde et al. (Long-Term Monitoring of Bacteria Undergoing Programmed Population Control in a Microchemostat, Science Jul. 1, 2005: vol. 309 No. 5731 pp. 137-140).*
Holtze et al. (Biocompatible surfactants for water-in-fluorocarbon emulsions, Lab Chip, 2008,8, 1632-1639, Sep. 2, 2008).*
Li et al. (Protein Crystallization Using Microfluidic Technologies Based on Valves, Droplets, and SlipChip, Annu Rev Biophys. 2010;39:139-58, Feb. 1, 2010).*
Brouzes et al. (Droplet microfluidic technology for single-cell high-throughput screening, Proc Natl Acad Sci U S A. Aug. 25, 2009;106(34):14195-200, Epub Jul. 15, 2009).*
VanderGheynst et al. (Design of formulations for improved biological control agent viability and sequestration during storage, Industrial Biotechnology, vol. 2 Issue 3: Oct. 17, 2006).*
VanderGheynst et al. (Water-in-oil emulsions that improve the storage and delivery of the biolarvacide Lagenidium giganteum, BioControl, Apr. 2007, vol. 52, Issue 2, pp. 207-229).*
International Search Report dated Nov. 16, 2011 in Application No. PCT/GB2011/051552.
International Preliminary Report on Patentability dated Feb. 26, 2013 in Application No. PCT/GB2011/051552.
UK Search Report dated Dec. 15, 2010 in UK Application No. GB1013969.9.

* cited by examiner

*Primary Examiner* — Aaron Priest
(74) *Attorney, Agent, or Firm* — Snell & Wilmer L.L.P.

(57) ABSTRACT

This invention relates to methods and systems for providing chemical and/or biological materials. Thus we describe a method of providing a chemical or biological material in a quantized form, the method comprising: preparing an emulsion comprising a plurality of microdroplets each holding a controlled amount of said material; storing said chemical or biological material in said microdroplets in said emulsion; transferring a portion of said emulsion microdroplets to a container for transportation; transporting said container to a user of said material, wherein said user receives said material in a quantized form in said microdroplets of said emulsion; and de-emulsifying said received microdroplets containing said material in quantized form to extract said material for subsequent use.

17 Claims, 1 Drawing Sheet

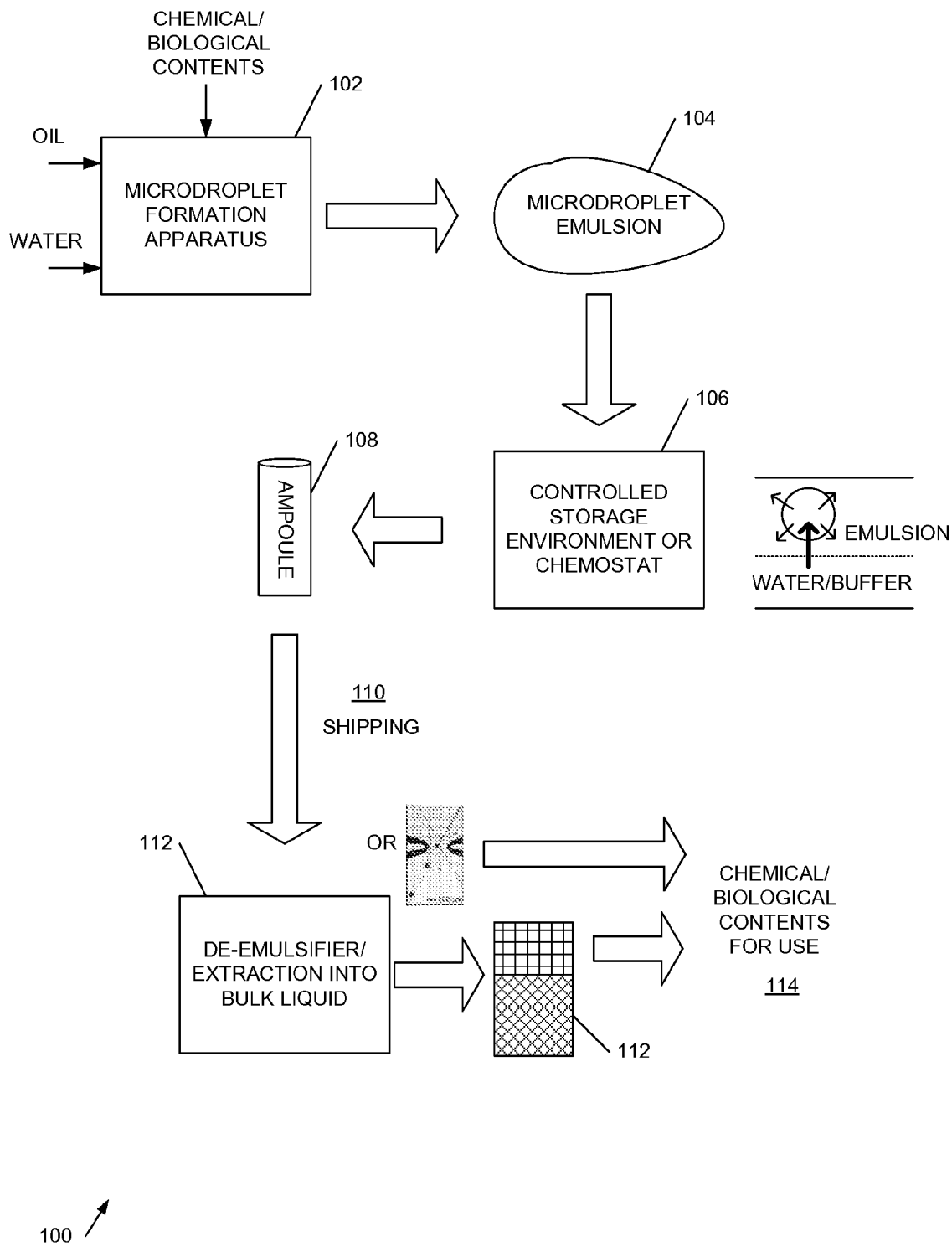

METHOD OF PROVIDING A CHEMICAL OR BIOLOGICAL MATERIAL IN QUANTISED FORM AND SYSTEM THEREFOR

CROSS-REFERENCE TO RELATED APPLICATIONS

This application is U.S. national phase filing under 35 U.S.C. §371 of PCT/GB2011/051552 filed on Aug. 17, 2011, and claims priority from United Kingdom Application No. GB 1013969.9 which was filed on Aug. 20, 2010, both of which are incorporated herein by reference.

FIELD OF THE INVENTION

This invention relates to methods and systems for providing chemical and/or biological materials.

BACKGROUND TO THE INVENTION

Microdroplets show great promise as a new high-throughput technology in chemistry, biochemistry and molecular biology. Microdroplets can be generated at rates in excess of several thousands per second and accurately formulated using minute amounts of small molecules, DNA, proteins or cells. Furthermore, integrated active elements can be used to control individual droplets. For example, we have previously described, in WO2009/050512, a technology that bridges the fields of microdroplets and continuous flow microfluidics by extracting on-chip the contents of microdroplets and incorporating them into a continuous stream.

Traditionally microdroplets have served as "microreactors" for controlled processing of the contents. For example, Rain Dance Technologies Inc, have technology to fuse microdroplets holding a specific primer pair with other microdroplets containing the DNA to which the specific primers are to be attached. Other background prior art can be found in US2010/0022414 and in US2010/0137163.

The inventors have recognised that microdroplets may, alternatively, be used in other ways.

SUMMARY OF THE INVENTION

According to the present invention there is therefore provided a method of providing a chemical or biological material in a quantised form, the method comprising: preparing an emulsion comprising a plurality of microdroplets each holding a controlled amount of said material; storing said chemical or biological material in said microdroplets in said emulsion; transferring a portion of said emulsion microdroplets to a container for transportation; transporting said container to a user of said material, wherein said user receives said material in a quantised form in said microdroplets of said emulsion; and de-emulsifying said received microdroplets containing said material in quantised form to extract said material for subsequent use.

The inventors have recognised that there are special problems in storage and handling of very small quantities of often high-value materials to which microdroplet technology can provide a solution. More particularly, microdroplets provide a method of handling very small amounts of material by encapsulating the material in a microdroplet in a quantized amount (for example molar or by weight), thus enabling a controlled quantity of the microdroplets to stored, transported, and dispensed, at the receiving end, de-emulsifying the droplets to extract the material for subsequent use, for example into a bulk liquid. In a synergistic manner, the use of microdroplets in an emulsion to store the chemical/biological material facilitates stable, long-term storage, in embodiments without affecting the controlled extraction of the material from the microdroplets. Thus, for example, whilst the volume of a microdroplet might change during storage thus effectively changing the concentration of material within the droplet, the actual quantized amount of material deposited by a single droplet remains substantially the same. Thus in embodiments by simply counting out a number of droplets a determined amount of material may be extracted into, say, a bulk liquid for subsequent processing.

Notwithstanding this, in embodiments of the method either or both of the storing and transporting may also include a compensatory process to, in effect, top-up liquid lost from a microdroplet by dissolution into the emulsion, to thereby substantially maintain droplet size and/or material concentration. In embodiments this may comprise semi-permeable membrane in contact with the emulsion against which top-up fluid is located, for example water or a buffer solution. In this way a substantially chemical/biological environment may be maintained.

In the case of a biological material, in particular a living biological material, microdroplets have the advantage of providing a substantially sterile environment. An arrangement broadly along the lines described above may be employed to provide an enhanced gaseous exchange environment for the biological material, for example to help maintain a level of oxygen within a microdroplet. For this purpose it is particularly preferable that a fluorous oil (eg a fluorocarbon or perfluorocarbon-based oil) is employed for the emulsion, as this can absorb oxygen and help to create an oxygen rich environment for a living biological material by transferring the oxygen from an external environment into the oil layer and through to the living material, which may comprise cells, bacteria, small organisms, algae and the like. Optionally nutrients for the living material may also be included in a microdroplet. In general a microdroplet storing living biological material comprises a droplet of aqueous fluid, for example water, in oil, or a double emulsion of (water in oil) in water may be employed.

In embodiments of the method where the material comprises entities such as cells, labelled beads, and the like preferably there is, on average, an integral number, for example unity, of entities in each microdroplet. Preferably most or all microdroplets include at least one entity (although this is not essential since the entities may be labelled so that the presence or absence of an entity may be detected and/or so that the number of dispensed entities may be counted, say, using a laser fluorescence process. Where labelled entities are stored in the microdroplets, in embodiments a label-detecting sorting device such as a FACS (fluorescence activated cell sorter) may be employed to enrich the emulsion, that is to increase a proportion of microdroplets holding at least one entity.

Where the material held within a microdroplet comprises a material in solution, preferably the microdroplets are substantially monodisperse, that is for example, having a polydispersity index of less than 0.1, in embodiments less than 0.05 (the polydispersity index may be defined, for an assumed Gaussian distribution, as $\sigma^2/x^2$ where the mean droplet size is x and the standard deviation of the distribution is $\sigma$). This is advantageous when a microdroplet holds the material in solution because preparing a substantially monodisperse microdroplet emulsion means that substantially the same amount of material is incorporated within each microdroplet.

Different types of emulsion may be employed depending, in part, upon the material to be transported. Thus the emulsion may comprise a water-in-oil emulsion, as previously described or a double emulsion such as a water-in oil-in water double emulsion, which is particularly advantageous for the storage of reagents. Alternatively the emulsion may comprise an emulsion of two (or more) immiscible organic liquids, which can be advantageous, for example, for storing/transporting chemical/biological catalyst material.

Embodiments of the above described technique are particularly advantageous for storage/shipping/handling of materials which are very expensive but may be provided/used in very small, sometimes invisible, amounts, such as antibodies. The storage/transportation/handling of such materials can otherwise be very difficult. It is important to recognise here that we are not describing microfluidic-type experiments in which processing is performed by, for example, fusing two different types of microdroplets containing materials which are to be reacted together; instead we are describing techniques for managing in general small quantities of high value material in which the material is afterwards extracted from the microdroplets, but in a controlled quantised manner, say into a bulk liquid, even where the actual amounts of the material are so small as to be substantially invisible.

Thus another application of embodiments of the above described techniques is the transportation of biological crystalline material, such as a protein crystal, to a synchrotron, for x-ray diffraction analysis or similar structural characterisation. Other applications include (but are not limited to) the transportation of radionucleotides such as phosphorous-32, and the transportation of catalysts, as previously mentioned. Although some preferred embodiments employ fluorous oil as one of the liquids of the emulsion, a hydrocarbon-based oil may additionally or alternatively be employed. In some preferred embodiments the microdroplets are stabilized by employing a surfactant, which may be either polymeric (for example with a hydrophilic core and fluorocarbon or hydrocarbon side chains) or non-polymeric (small molecule).

The amount of material within a microdroplet may, in embodiments, be less than 100 nm, 10 nm or 1 nm. Optionally when the microdroplets are being prepared, the preparation process may include splitting a droplet into two, three or more, which may be achieved using geometrical flow techniques, for example a T-junction to divide droplets into two.

The de-emulsifying process may simply comprise adding an excess of a fluid such as oil and/or adding a de-emulsifying agent to split the emulsion into separate bulk phases, for example water and oil. Thus in embodiments the de-emulsification process to extract the contents of a microdroplet or microdroplets is not performed in a microfluidic device. Optionally the de-emulsification process may comprise blending the contents of two different types of microdroplets into a common bulk liquid phase.

The skilled person will recognise that different parts of the above described method may be implemented by different users of the method, in particular at the preparation end of the process, and at the material use end of the process.

Thus in a first related aspect there is provided a method of preparing a chemical or biological material for providing to a user in a quantised form, the method comprising: preparing an emulsion comprising a plurality of microdroplets a holding a controlled amount of said material; storing said chemical or biological material in said microdroplets in said emulsion; and transferring a portion of said emulsion microdroplets to a container for transportation; wherein said user receives said material in a quantised form in said microdroplets of said emulsion on receipt of said container.

The user receiving the shipped droplets may use the microdroplets in a number of ways including (but not limited to): 1) Using the droplets neat, that is without de-emulsification; 2) diluting or concentrating the droplets without de-emulsification; 3) de-emulsifying the droplets to access the contents.

In a further related there is provided a method of receiving a chemical or biological material in quantised form, the method comprising: receiving from a supplier of said chemical or biological material a container holding an emulsion comprising a plurality of microdroplets each holding a controlled amount of said material, such that said user receives said material in a quantised form in said microdroplets of said emulsion; and de-emulsifying said received microdroplets containing said material in quantised form to extract said material for subsequent use.

The skilled person will recognise that features and aspects of the above described embodiments of the complete end-two-end method may be employed with the above described portions of the method implemented at either end of the complete procedure.

In a related aspect the invention provides a system for providing a chemical or biological material in quantised form, the system comprising: apparatus configured to prepare an emulsion comprising a plurality of microdroplets each holding a controlled amount of said material; apparatus to store said chemical or biological material in said microdroplets in said emulsion to a user; apparatus to transfer a portion of said emulsion microdroplets to a container for transportation to a user; wherein said user receives said material in a quantised form in said microdroplets of said emulsion; and apparatus to de-emulsify said received microdroplets containing said material in quantised form to extract said material for subsequent use.

The invention further provides apparatus for preparing a chemical or biological material for providing to a user in a quantised form, the apparatus comprising: apparatus configured to prepare an emulsion comprising a plurality of microdroplets each holding a controlled amount of said material; apparatus to store said chemical or biological material in said microdroplets in said emulsion to a user; and apparatus to transfer a portion of said emulsion microdroplets to a container for transportation to a user, wherein said user receives said material in a quantised form in said microdroplets of said emulsion.

The invention still further provides apparatus for receiving a chemical or biological material in quantised form, the apparatus comprising: a container from a supplier of the chemical or biological material, the container holding an emulsion comprising a plurality of microdroplets each holding a controlled amount of said material; and apparatus to de-emulsify said received microdroplets containing said material in quantised form to extract said material for subsequent use.

Again features and aspects of the previously described methods may be implemented into apparatus configured to implement the methods. For the sake of brevity these will not be repeated here, but the skilled person will understand that the invention also contemplates means for performing the various features and aspects of the previously described methods. Thus, for example, there may be provided apparatus to maintain a gaseous environment within the microdroplets and/or to compensate for loss of liquid from the microdroplets to the emulsion; this apparatus may be incorporated into the container transporting the microdroplet emulsion. Similarly apparatus may be provided to facilitate extracting a controlled quantity of microdroplets from the container, for example by counting out a number of microdroplets.

According to a further aspect of the invention there is provided a method of protecting cells or other living entities or a reagent in a device, the method comprising: forming an emulsion comprising microdroplets of an aqueous medium in oil, wherein said cells or other living entities or reagent are provided in said microdroplets; and processing said cells or reagent in said device protected with said microdroplets.

According to another aspect there is also provided apparatus for protecting cells or a reagent in a device, the apparatus comprising: means for forming an emulsion comprising microdroplets of an aqueous medium in oil, wherein said cells or other living entities or reagent are provided in said microdroplets; and means for processing said cells or reagent in said device protected with said microdroplets.

In embodiments the method/apparatus may also provide nutrients for the cells or other living entities in the microdroplets; a fluorous oil may be employed to provide an enhanced gaseous exchange environment for the cells or other living entities. Alternatively a fluorous oil may be employed to provide an oxygen deficient environment to facilitate storage of a reagent. Optionally a reagent may be concentrated within the microdroplets during preparation of the emulsion. These techniques may also be employed with the methods previously described.

There is also provided a method/apparatus of/for growing a cell or other living entity, wherein the cell or other living entity is held within an aqueous droplet in oil, in particular in conjunction with a nutrient.

BRIEF DESCRIPTION OF THE DRAWINGS

These and other aspects of the invention will now be further described, by way of example only, with reference to the accompanying figures in which:

FIG. 1 shows, schematically, an example of a method according to an embodiment of the invention.

DETAILED DESCRIPTION OF PREFERRED EMBODIMENTS

Microdroplet Protected Storage

Various "reagents" can be stored in droplets. These include:

Organisms: such as *C. elegans*, zebrafish embryos, *D. melanogaster* lavae etc.

Tissues: including extracts, secretions, samples or biopsies.

Cells: including mammalian, bacteria, yeast, fungal, protozoan and algae.

Parasites: such as viruses, plasmids, transposons and prions.

Macromolecular structures and complexes (synthetic): such as polymers, beads (paramagnetic and other), buckminsterfullerene, nanotubules and gels.

Macromolecular structures and complexes (natural): polymers, gels, genes, vectors, membranes.

Biological fluids: such as blood, serum, semen, seminal fluid, nipple aspirate, nasal secretions, sweat, tears, bile, conjunctival fluid, cerebrospinal fluid, urine, mestrual fluid, organ fluids, breath aspirate, saliva, faecal extracts.

Molecules: lipids, nucleic acids, carbohydrates, drugs, chemicals, compounds, ions, elements, drugs, analytes, proteins, enzymes, antibodies, peptides, lipids, nucleic acids, metabolites, carbohydrates, glycoproteins and catalysts.

Ions: including $Mg^2$, $Cl^-$, and the like.

Gases: such as $CO_2$, $O_2$, and the like.

These reagents can be stored, dispensed and delivered in various microdroplet types. The microdroplet contents may be in a water-oil emulsion or a water-oil-water emulsion (a double emulsion) or variants thereof that could be comprised of different oils. Various surfactants may also be used to stabilise microdroplet interfaces.

The microdroplet format has the unexpected effect of stabilising stored reagents preventing them from biological, chemical or physical deterioration. Microdroplets also have a large surface area for their volume which is good for gas exchange—this can help with cell survival such that they survive for many days. The use of fluorous oils can also help $O_2$ to dissolve, which can be useful for applications which require oxygen-rich environments, by providing an external source of oxygen—and "in reverse" oxygen-deficient environments, by providing an external oxygen sink. Thus the use of fluorous oils can also be useful for applications which require oxygen-deficient environments.

In addition, by storage of such reagents in droplets, this can improve the utilisation of the stored reagent by enabling the dispensing of one or more small droplets (a volume range including but not restricted to picoliters through to nanoliters) into an assay in a format which prevents evaporation of the enclosed solvent(s) of the droplet. Evaporation of a solvent can cause subsequent damage to the reagent as it causes dehydration of the reagent; this effect is inhibited by the use of microdroplets.

The use of oil-water droplet emulsions and double emulsions has the unexpected property that it can stabilise any encapsulated reagents during storage and dispensing. Also, as the droplet format can concentrate the reagent within the droplet solution, this can also have a protective effect on certain reagents. For example, some reagents are known to become inactive at low concentration upon storage due to effects such as absorption to storage vessel walls. Storage of the reagents in a droplet format reduces this effect.

Also, during reagent dispensing, certain reagents can suffer from physical shear stress during the movement process or adsorb to the wall of the dispenser and the reagents thus lose activity. By dispensing the reagents in a droplet format, this shear stress and adsorption effect is reduced.

The inventors have observed that emulsion droplets have applications as stabilising reagents, prolonging their function and cell survival, reducing shear stress, adsorption of reagents and their damage during dispensing.

Droplet production can be done using easily purchasable equipment from well-known suppliers. The chemicals and surfactants desired for droplet production are also easily available. An engineering system which automates the large-scale production of reagents in droplets may be provided.

Stable, Quantised Material Storage and Transportation

Broadly speaking we will describe a system which allows the generation of microdroplets having contents, the storage and transfer of the generated microdroplets, and dispensing of the microdroplet contents. Thus embodiments use microdroplets as storage, delivery and/or dispensing agents. The system is generally concerned with manipulating microdroplets rather than, more specifically, the contents thereof. Embodiments of the system are therefore not concerned with microfluidics as such, although the contents may be delivered by a microfluidic device.

The storage is of an emulsion comprising the generated microdroplets. This may comprise an oil in water, water in oil, organic solvent in oil, or the like, emulsion. Generally, the microdroplets may have volumes of the order of pL to nL (eg <10 nL or <1 nL). A microdroplet may have a maximum lateral dimension of less than 1 mm, 500 µm, 100 µm, 50 µm, 10 µm, or 1 µm.

The generation of microdroplets with contents, e.g., a reagent, may involve putting the contents into the microdroplets. The generation may optionally further involve generating the microdroplets prior to adding the contents, which may be achieved for example by membrane emulsification, a microdroplet sorter and/or flow focussing device, and/or by diluting a suspension of cells (or other content material) and screening out microdroplets that remain empty, i.e., which do not contain cells (or other biological/labelled entities). Microdroplets may be created using microfluidics (channel width <1000 μm, for example ~100 μm), but thereafter the microdroplets may be harvested, removed from the microfluidics chip and then stored and shipped and dispensed using other formats or containers.

The microdroplets with or without the contents may be polydisperse but more preferably, for example for accurate determination of the amount of content dispensed, the microdroplets are substantially monodisperse (the microdroplets have the substantially the same size, e.g., have monodispersity of less than about 5%, e.g., less than or equal to ~1 to ~2%).

The contents of the stored microdroplets may comprise different contents in different respective microdroplets. For example, the storage may store mutually reactive components separately in respective microdroplets, the reaction taking place after storage, from example upon de-emulsification. Thus, the microdroplets may have the same or different contents, and the different contents may be present in the emulsion in various ratios.

The emulsion may be stored in a vial, syringe, tubing, Eppendorf pipette, or glass capsule containing an emulsion comprising the microdroplets. Preferably, however, the storage unit functions as a chemostat, for example a microscopic chemostat for storing microdroplets for days, weeks or months. In such a chemostat, nutrients may be transferred, for example to promote growth of a biological organism in a microdroplet. The chemostat may comprise a membrane between an outer water layer and the oil of the emulsion. Such a membrane may reduce or substantially prevent shrinkage of an aqueous microdroplet in the oil, which otherwise may reduce in size due to diffusion of water from the microdroplet into the oil. Preferably, the chemostat maintains a constant chemical environment for the microdroplet and/or content, this being advantageous for example for maintenance of life of a biological entity. Such maintenance of life generally requires gaseous input and output (e.g. $O_2$) which may be achievable using fluorous oil as the microdroplet carrier of the emulsion. A double emulsion may similarly be advantageous for such maintenance of life.

However, such shrinkage of microdroplets may allow a constant concentration of the microdroplet contents to be maintained in the emulsion and therefore the use of a chemostat and/or double emulsion or the like is not essential. Therefore, a single emulsion may be used rather than a double emulsion. In this regard, it is noted that a double emulsion may be processable by a FACS (fluorescence-activated cell sorter) machine, which may be used to enrich the microdroplets before shipping, e.g., to ensure that substantially the droplets contain the desired content, e.g., cell(s), microspheres or microbeads as a chemical/biological material, for example DNA, carrier, and the like.

The transfer may comprise shipping, e.g., by post, by any means, e.g., flight, ship, haulage, etc. and may be across long distances, e.g., inter-state or further. An embodiment may comprise shipping a chemostat containing the microdroplets.

The dispensing may involve counting or measuring a predetermined amount and de-emulsifying. For example, a predetermined number of one or more of the microdroplets may be counted out, e.g., by a FACS sorter device. Additionally or alternatively, a device that is separate or integrated to the storage unit may be used to perform the counting, e.g., using a laser to count the microdroplets as the emulsion flows out of the storage. Alternatively, the dispensing may be achieved by measuring out a volume of the emulsion, e.g., of the order of mL. Thus, an embodiment may contrast with typically dispensation on a weight or volume basis, e.g., on the basis of mg or mL quantities of contents which are not first provided in microdroplets.

Thus, since the contents are quantized on a per-microdroplet basis dispensing of a defined number of microdroplets may be achievable, the dispensing may advantageously dispense very small quantities of the required contents, e.g., as contained within 1, 10, 100, or 1000 microdroplets. The fine granularity with which quantities of the content may be dispensed may allow delivery of very small quantities, e.g., for adding small amounts of a chemical and/or biological entity to an experiment.

The de-emulsifying is generally performed by destablising the emulsion to break up the microdroplets, for example by adding fluorous oil such that the emulsion effectively disappears leaving behind the microdroplets. Various other de-emulsifying methods may be additionally or alternatively be used, however, e.g., adding salt and/or surfactant to lyse the microdroplets, shearing, heating, sonification, and so forth.

In an alternative approach, we have previously described, in WO2009/050512 (incorporated by reference) how extraction may be achieved through electrocoalescence: droplets are forced to coalesce with an aqueous stream by applying an electric field across the channel. The extraction is controlled through a voltage applied at microfabricated electrodes on each side of the channel and can be performed in a continuous or discrete fashion, optionally triggered by an external electrical signal. This may be in response to the contents of the droplets (for example based on a detected fluorescence intensity) resulting in a system capable of selectively incorporating the contents of droplets of interest to a continuous microfluidic stream.

The stored microdroplets may be divided, for example by dispensing a fraction, e.g., ½, ⅓, ¼, etc. of the emulsion or counting out some of the microdroplets, and/or on a sub-microdroplet basis by splitting. Such splitting may be achieved by pushing microdroplets up against a wall in a flow path of emulsion containing the microdroplets, the volume ratio of splitting each microdroplet into parts (e.g., 1:1, 1:2, 1:3, etc.) depends on the geometry of the flow path, for example a T-junction.

Advantageously, the microdroplets provide a sterile environment for the stored contents. Additionally or alternatively, the storage of contents in the microdroplets may allow the microdroplets to be kept in an aqueous environment. This may extend the length of time during which the contents can be preserved without significant deterioration.

The contents of the stored microdroplets may comprise biopharma compositions or biological entities such as DNA, protein, peptide, bacteria, small multi-cell organism(s) (e.g., embryos), single cell(s), spore(s), antibody(s), etc. For example, entities, e.g., proteins, that may otherwise be damaged by hydration followed by dehydration are advantageously stored, transferred and dispensed by an embodiment, which allows the transfer and storage to take place while the entity remains in the aqueous environment of the microdroplet.

Example applications include drug delivery and biological and/or chemical laboratory experiments. However, embodiments are applicable and advantageous in numerous fields. For example, contents which typically need dispensing in very small quantities are dye molecules, crystals or microcrystals for synchrotrons, radio isotopes, and catalysts, e.g., for curing materials such as PDMS (Polydimethylsiloxane). Examples of contents which are typically need storage and dispensing in a secure environment and/or in small quantities are tuberculosis strains and nanoparticles (i.e., organic or inorganic particles of dimension less than about 100 nm). Embodiments may be advantageous for storing and dispensing toxic entities.

One important advantage of the above-described techniques is that they facilitate the combination of microdroplets-based techniques with microfluidic analytical devices. In general microfluidic analytical devices will not work satisfactorily with a stream of emulsion as oil affects the operation of such devices. The above described techniques enable the contents of a droplet to be separated from the oil so efficiently that the resulting stream of aqueous solution is as if the materials carried by the solution have never been in an emulsion in the first place. Further, the aqueous stream may be employed to functionally process the contents of a droplet, for example by cleaving a material such as DNA from a solid support such as a microsphere. The skilled person will appreciate that the above techniques may be employed for a very wide variety of chemical and biological procedures including, but not limited to, the processing and analysis of DNA, proteins, cells, enzymes, antigens and the like, in particular, in high-throughput systems, as well for other chemical and/or biological reactions and processes, for example PCR (polymerase chain reaction), and in a wide variety of sensors and detectors, for example for detecting biological, chemical or radiological threats.

Referring to FIG. 1, this shows an embodiment of a system 100 according to the invention. The system comprises microdroplet formation apparatus 102, as illustrated forming a water-in-oil emulsion 104 of microdroplets containing the chemical/biological contents, which is provided to a controlled storage environment apparatus 106 or chemostat. In embodiments the chemostat comprises a water/buffer solution in contact with a membrane which is in turn in contact with the emulsion, as illustrated in the inset drawing. When desired some or all of the contents of the storage apparatus are transferred to an ampule 108 for shipping 110 to a end user who has de-emulsification apparatus 112 which may either lyse the microdroplets into one phase of two separate water/oil layers, or which may comprise apparatus as previously described in WO'512 (Ibid) to capture droplets into an aqueous stream. In either approach the chemical/biological contents are extracted into a bulk liquid for subsequent processing/use.

No doubt many other effective alternatives will occur to the skilled person. For example in embodiments/aspects of the invention step of the method may be combined. It will be understood that the invention is not limited to the described embodiments and encompasses modifications apparent to those skilled in the art lying within the spirit and scope of the claims appended hereto.

The invention claimed is:

1. A method of providing a chemical or biological material in a quantised form, the method comprising:
preparing an emulsion comprising a plurality of microdroplets,
wherein each of said plurality of microdroplets holds a controlled amount of said material,
wherein one or more said microdroplets comprises a first liquid,
wherein said microdroplets are suspended in a second liquid to form said emulsion;
storing said chemical or biological material in said microdroplets in said emulsion;
providing a semi-permeable membrane in contact with said emulsion against which top-up fluid is located for performing a compensating process;
performing said compensating process to return said first liquid to an interior of said microdroplet to compensate for loss of said first liquid to said second liquid of said emulsion in which said microdroplet is suspended; and
de-emulsifying said microdroplets containing said material in quantised form to extract said material for subsequent use.

2. The method as claimed in claim 1, wherein said emulsion is a double emulsion.

3. The method as claimed in claim 1, wherein said emulsion comprises a fluorous oil, the method further comprising controlling gaseous movement through said fluorous oil to control an internal environment of said microdroplet.

4. The method as claimed in claim 1, wherein said de-emulsifying further comprises blending contents of two different types of said microdroplets holding different types of said material into a common bulk liquid phase.

5. The method as claimed in claim 1, wherein said preparing comprises dividing microdroplets of said emulsion into two or more smaller microdroplets.

6. The method as claimed in claim 1, wherein said quantised form of said material comprises quantisation of said material into amounts of less than 100 nM, 10 nM or 1 nM.

7. The method as claimed in claim 1, wherein said microdroplet holds said material in solution within said microdroplet, and wherein said preparing comprises preparing an emulsion wherein said microdroplets are substantially monodisperse.

8. The method as claimed in claim 7, wherein a change in a volume of said microdroplet while said chemical or biological material is held within said microdroplet changes a concentration of said material within said microdroplet but does not substantially affect the quantised amount of said material provided by de-emulsifying a controlled quantity of said microdroplets.

9. The method as claimed in claim 1, wherein said material comprises living biological entities, wherein said first liquid in said microdroplet provides a sterile environment for said living biological entities, and wherein said microdroplets each hold, on average, substantially an integral number of said living biological entities.

10. The method as claimed in claim 1, wherein said material comprises labelled entities, and wherein said preparing includes using a label-detecting sorting device to sort said microdroplets to increase a proportion of said microdroplets holding one or more of said labelled entities.

11. The method as claimed in claim 1, wherein said emulsion of said microdroplets comprises an emulsion of two immiscible organic liquids.

12. The method as claimed in claim 1, wherein said material comprises a crystalline material for structural characterisation, the method further comprising providing said material for synchrotron radiation analysis.

13. A method of providing a chemical or biological material in a quantised form, the method comprising:
preparing an emulsion comprising a plurality of microdroplets,
wherein each of said plurality of microdroplets holds a controlled amount of said material,
wherein said microdroplet comprises a first liquid,
wherein said microdroplets are suspended in a second liquid to form said emulsion;

storing said chemical or biological material in said microdroplets in said emulsion,
providing a semi-permeable membrane in contact with said emulsion against which top-up fluid is located for performing a compensating process; and
performing said compensating process to return said first liquid to an interior of said microdroplet to compensate for loss of said first liquid to said second liquid of said emulsion in which said microdroplet is suspended.

14. The method as claimed in claim 1 further comprising:
receiving from a supplier of said chemical or biological material a container holding said emulsion comprising a plurality of said microdroplets, wherein each microdroplet holds a controlled amount of said stored chemical or biological material, such that said user receives said material in said quantised form in said microdroplets of said emulsion, wherein said de-emulsifying comprises de-emulsifying said received micro-droplets.

15. The method as claimed in claim 1, further comprising:
transferring a portion of said emulsion microdroplets to a container for transportation;
storing said chemical or biological material in said microdroplets in said emulsion, and
transporting said container to a user of said material, wherein said user receives said material in a quantised form in said microdroplets of said emulsion;
wherein said de-emulsifying comprises de-emulsifying said received microdroplets.

16. The method as claimed in claim 15, further comprising extracting a controlled quantity of said microdroplets from said container.

17. The method as claimed in claim 16, wherein said extracting comprises counting a number of said microdroplets to determine said quantity.

* * * * *